United States Patent [19]

Eicken et al.

[11] Patent Number: 4,808,211

[45] Date of Patent: Feb. 28, 1989

[54] N-ARYLSULFONYL-N'-PYRIMIDYL UREAS

[75] Inventors: Karl Eicken, Wachenheim; Peter Plath, Frankenthal; Bruno Wuerzer, Otterstadt; Norbert Meyer, Ladenburg, all of Fed. Rep. of Germany

[73] Assignee: BASF Aktiengesellschaft, Ludwigshafen, Fed. Rep. of Germany

[21] Appl. No.: 116,902

[22] Filed: Nov. 5, 1987

[30] Foreign Application Priority Data

Nov. 20, 1986 [DE] Fed. Rep. of Germany ....... 3639563

[51] Int. Cl.$^4$ ............... C07D 239/69; C07D 409/14; C07D 401/04; A01N 43/54
[52] U.S. Cl. .................................. 71/92; 71/90; 544/320; 544/321; 544/324; 544/331
[58] Field of Search .............. 71/90, 92; 544/320, 544/321, 324, 331

[56] References Cited

FOREIGN PATENT DOCUMENTS 0007687 3/1983 European Pat. Off. .

OTHER PUBLICATIONS

Levitt (1982) Pesticide Chemistry 1: 243–250, Proceedings of IUPAC Congress, Kyoto.

Primary Examiner—John M. Ford
Attorney, Agent, or Firm—Keil & Weinkauf

[57] ABSTRACT

Novel N-arylsulfonyl-N'-pyrimidyl-ureas of the formula

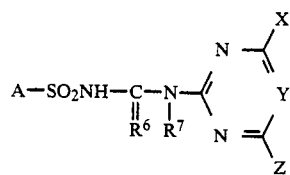

where A is a radical of the formula

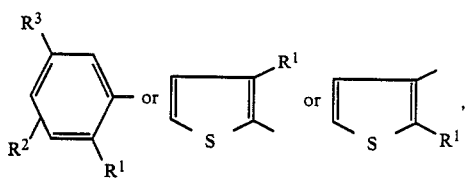

where
$R^1$ is hydrogen, halogen, cyano, nitro, haloalkyl, alkyl, alkoxy, CO-$R^4$, S(O)$_m$-alkyl or SO$_2R^5$,
$R^2$ is hydrogen, halogen, methyl, ethyl, methoxy or ethoxy,
$R^3$ is hydrogen, halogen, nitro or methoxy,
$R^4$ is hydrogen, alkyl, alkoxy, alkenyloxy, alkynyloxy, alkylthio, phenoxy, benzyloxy or alkoxy which is unsubstituted or substituted by halogen atoms or alkoxy,
$R^5$ is alkoxy, phenoxy or benzyloxy which is unsubstituted or substituted by 1 to 3 halogen atoms,
m is one of the integers 0, 1 and 2,
$R^6$ is oxygen or sulfur,
$R^7$ is hydrogen or alkyl,
X is alkyl, haloalkyl, alkoxy, haloalkoxy, alkylthio or halogen,
Y is the methyne group -CH and
Z is azolyl linked via nitrogen, salts of these compounds, and their use for combating the growth of unwanted plants.

8 Claims, No Drawings

N-ARYLSULFONYL-N'-PYRIMIDYL UREAS

The present invention relates to novel substituted N-arylsulfonyl-N'-pyrimidyl(triazinyl)ureas and their use for controlling undesirable plant growth. The present invention furthermore relates to novel aminopyrimidines and aminotriazines prepared as intermediates.

A number of patent applications disclose that sulfonylureas have herbicidal activity. It is also known that sulfonylureas which carry dimethylamino groups in the pyrimidine radical do not possess herbicidal activity (G. Levitt in Miyamoto and Kearney, Pesticide Chemistry Vol. 1, page 243 et seq. Proceedings of IUPAC Congress, Kyoto 1982).

We have found that N-arylsulfonyl-N'-pyrimidyl-(triazinyl)ureas of the formula

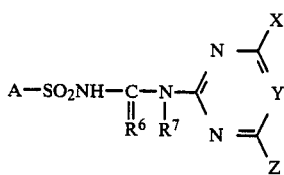
(I)

where A is a radical of the formula

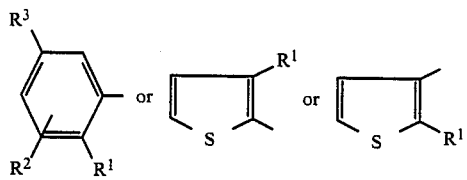

wherein $R^1$ is hydrogen, halogen, cyano, nitro, $C_1$–$C_4$-haloalkyl, $C_1$–$C_4$-alkyl, $C_1$–$C_4$-alkoxy, CO—$R^4$, S(O)$_m$—$C_1$–$C_4$-alkyl or SO$_2R^5$, $R^2$ is hydrogen, halogen, methyl, ethyl, methoxy or ethoxy, $R^3$ is hydrogen, halogen, nitro or methoxy, $R^4$ is hydrogen, $C_1$–$C_4$-alkyl, $C_1$–$C_5$-alkoxy, $C_3$–$C_5$-alkenyloxy, $C_3$–$C_5$-alkynyloxy, $C_1$–$C_5$-alkylthio, phenoxy, benzyloxy, or $C_1$–$C_5$-alkoxy which is unsubstituted or substituted by 1 to 3 halogen atoms or by $C_1$–$C_3$-alkoxy, $R^5$ is phenoxy, benzyloxy or $C_1$–$C_4$-alkoxy, which is unsubstituted or substituted by 1 to 3 halogen atoms, m is 0, 1 or 2, $R^6$ is oxygen or sulfur, $R^7$ is hydrogen or $C_1$–$C_3$-alkyl, X is $C_1$–$C_3$-alkyl, $C_1$–$C_3$-haloalkyl, $C_1$–$C_3$-alkoxy, $C_1$–$C_3$-haloalkoxy, $C_1$–$C_3$-alkylthio or halogen, Y is the methine group —CH= or nitrogen and Z is azolyl bonded via nitrogen, and salts of these compounds have advantageous herbicidal activity, particularly in the post-emergence method, and are selective with respect to a number of crops.

According to the number of carbon atoms, substituents of the radicals A of the general formula I are as follows: alkyl is, for example, methyl, ethyl, n-propyl, isopropyl or one of the four isomeric butyl radicals; alkoxy is, for example, methoxy, ethoxy, n-propoxy, isopropoxy, one of the four isomeric butoxy radicals, n-amyloxy, isoamyloxy, 2-amyloxy or 3-amyloxy, in particular methoxy, ethoxy or isopropoxy; alkylthio is, for example, methylthio, ethylthio, n-propylthio, isopropylthio, n-butylthio or n-pentylthio, in particular methylthio and ethylthio; alkenyloxy is, for example, allyloxy, isopropenyloxy, 1-propenyloxy, 1-butenyloxy, 2-butenyloxy, 3-butenyloxy, 1-isobutenyloxy, 2-isobutenyloxy, 1-pentenyloxy, 2-pentenyloxy, 3-pentenyloxy or 4-pentenyloxy, in particular 4-pentenyloxy; alkylsulfinyl is, for example, methylsulfinyl, ethylsulfinyl, n-propylsulfinyl or n-butylsulfinyl, in particular methylsulfinyl or ethylsulfinyl; alkylsulfonyl is, for example, methylsulfonyl, ethylsulfonyl or n-propylsulfonyl, in particular methylsulfonyl or ethylsulfonyl, and alkynyloxy is, for example, propargyloxy, 2-butynyloxy, 3-butynyloxy or one of the isomeric pentynyloxy radicals, preferably propargyloxy, 2-butynyloxy or 3-butynyloxy.

Halogen as substituent $R^1$, $R^2$ or $R^3$ and in the haloalkyl or haloalkoxy radicals may be fluorine, chlorine or bromine, preferably fluorine or chlorine.

Suitable azolyl radicals Z are pyrazolyl, 1,2,4-triazolyl, 1,2,3-triazolyl and imidazolyl.

The present invention likewise relates to the salts which the N-arylsulfonyl-N'-pyrimidyl(triazinyl)ureas of the formula I are capable of forming with amines, alkali metal bases, alkaline earth metal bases or quaternary ammonium bases.

The compounds of the formula I are obtainable by three methods:

(a) The compounds of the formula I are obtained by reacting an arylsulfonyl isocyanate or isothiocyanate of the formula

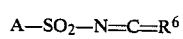
(II)

with an aminopyrimidine or aminotriazine of the formula

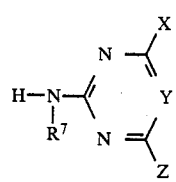
(III)

in the presence or absence of a base, in a conventional manner.

(b) In a second process, the compounds of the formula I can be prepared by reacting an arylsulfonamide of the formula

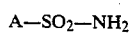
(IV)

with an N-pyrimidyl(triazinyl)-(thio)carbamate of the formula

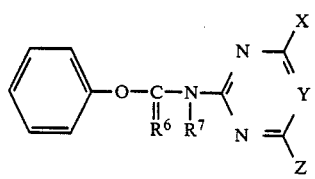
(V)

in the presence of a base, in a conventional manner.

(c) The compounds of the formula I are furthermore obtained by reacting an N-arylsulfonyl(thio)carbamate of the formula

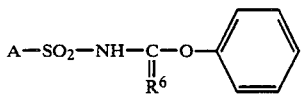 (VI)

with an aminopyrimidine or aminotriazine of the formula III in a conventional manner.

The ureas of the formula I which are obtained by this process may, if desired, be converted to addition salts by means of amines, alkali metal hydroxides, alkaline earth metal hydroxides or quaternary ammonium bases. This is carried out, for example, by reaction with an equimolar amount of the base and evaporation of the solvent.

All three processes are advantageously carried out in an aprotic, inert, organic solvent, methylene chloride, tetrahydrofuran, acetonitrile, dioxane and toluene being suitable.

The reaction temperatures are preferably from −20° to +120° C. The reactions are in general slightly exothermic and can readily be carried out at room temperature. To reduce the reaction time or to initiate the reaction, the reaction mixture is advantageously heated to its boiling point for a short time. The reaction times can also be reduced by adding a few drops of base or isocyanate as a reaction catalyst.

Suitable bases are both organic bases, such as amines, eg. triethylamine, quinuclidine, pyridine, etc., and inorganic bases, such as hydrides, eg. sodium hydride or calcium hydride, hydroxides, eg. sodium hydroxide or potassium hydroxide, carbonates, eg. sodium carbonate or potassium carbonate, or bicarbonates, eg. potassium bicarbonate or sodium bicarbonate.

The end products can be isolated by concentration and/or evaporation of the solvent and purified by recrystallization or trituration of the solid residue in solvents in which the end products are not readily soluble (ethers, aromatic hydrocarbons or chlorohydrocarbons). The compounds of the formula I are stable.

The intermediates of the formulae II, IV and VI are known or can be prepared by processes similar to the known ones.

The aminopyrimidines and aminotriazines of the formula III are novel. They were developed specially for the synthesis of the active ingredients of the formula I and therefore constitute a further subject of the present invention.

The compounds of the formula III are obtained by reacting an aminopyrimidine or aminotriazine of the formula

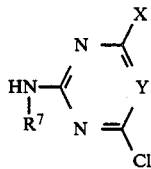 (VII)

with an azole or an alkali metal salt of an azole in the presence of a base.

The process for the preparation of the compounds of the formula III is advantageously carried out in an inert polar solvent or solvent mixture. Suitable solvents are ethers, such as dioxane, tetrahydrofuran, ethylene glycol dimethyl ether or diethylene glycol dimethyl ether, alcohols, such as methanol or ethanol, ketones, such as acetone or ethyl methyl ketone, dimethylformamide, acetonitrile or dimethyl sulfoxide.

Particularly suitable bases are sodium hydride, calcium hydride, potassium hydroxide, sodium hydroxide, potassium carbonate and sodium carbonate. In suitable cases, the base may be added in the form of an aqueous solution. The amount of base is not less than the molar amount of azole.

The starting compounds of the formula VII are known or are obtainable similarly to known processes.

The N-pyrimidyl)triazinyl)-(thio)carbamates of the formula V are likewise novel. They can be prepared from the compounds of the formula III by a process similar to the known ones.

PREPARATION EXAMPLES

1. N-(2-methoxycarbonylphenylsulfonyl)-N'-[4-methyl-6-(1',2',4'-triazol-1'-yl)pyrimid-2-yl]urea (a) 3.5 g of sodium hydride (80%) are introduced a little at a time into a solution of 7.6 g of triazole in 80 ml of dimethylformamide at 10° C. When evolution of gas has ceased, 14.4 g of 2-amino-4-methyl-6-chloropyrimidine, dissolved in 60 ml of warm dimethylformamide, are added, and stirring is carried out for 3 hours at 100° C. The solvent is evaporated, the residue is made into a paste with water and recrystallization is carried out from dimethylformamide, after which 11.8 g of 2-amino-4-methyl-6-(1',2',4'-triazol-1'-yl)pyrimidine of melting point 278°–280° C. are isolated.

(b) A solution of 8.6 g of 2-methoxycarbonylphenylsulfonyl isocyanate in 10 ml of dry tetrahydrofuran is added dropwise to a suspension of 6.3 g of the above pyrimidine in 70 ml of dry tetrahydrofuran and 15 mg of diazabicyclooctane. When the slightly exothermic reaction has died down, the mixture is stirred overnight at room temperature. The precipitate is filtered off under suction and washed with 10 ml of tetrahydrofuran, after which 12.6 g of N-(2-methoxycarbonylphenylsulfonyl)-N'-(4-methyl-6-(1',2',4'-triazol-1'-yl)pyrimid-2-yl-urea of melting point 227°–230° C. (compound no. 2.09) are isolated.

2. N-(2-chlorophenylsulfonyl)-N'-(4-pyrazol-1'-yl-6-methoxytriazin-2-yl)urea (a) 2.7 g of sodium hydride (80%) are introduced a little at a time into a solution of 6.1 g of pyrazole in 60 ml of dimethylformamide at 10° C. and, when evolution of gas has ceased, 13.0 g of 2-amino-4-chloro-6-methoxytriazine are added all at once, while cooling with ice. When the slightly exothermic reaction has died down, stirring is continued for a further hour at 40° C. and the solvent is then removed under reduced pressure. The residue is made into a paste with a little ice water, the pH is brought to 4–5, the mixture is filtered under suction and the product is dried under reduced pressure to give 8.0 g of 2-amino-4-pyrazolo-6-methoxytriazine of melting point 154°–157° C. (decomposition).

(b) A solution of 2-chlorophenylsulfonyl isocyanate in 10 ml of dry acetonitrile is added dropwise to a suspension of 3.9 g of the above triazine in 70 ml of dry acetonitrile and 15 mg of diazabicyclooctane. When the slightly exothermic reaction has died down, the mixture is stirred for 3 hours at 50° C. After the mixture has been cooled and filtered under suction, 3.5 g of N-(2-chlorophenylsulfonyl)-N'-(4-pyrazol-1'-yl-6-methoxytriazin-2-yl)urea of melting point 180°–182° C. (compound no. 2.24) are isolated.

The compounds of the formulae I and III which are stated in the Tables below can be prepared in a similar manner:

TABLE 1

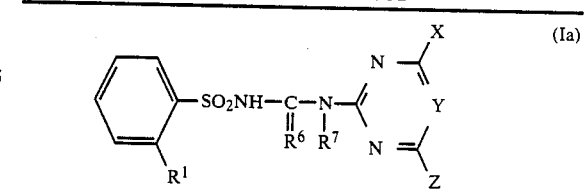
(III)

| Comp. no. | R⁷ | X | Y | Z | M.p. [°C.] |
|---|---|---|---|---|---|
| 1.01 | H | $CH_3$ | CH | pyrazolyl | 155-156 |
| 1.02 | H | $OCH_3$ | CH | pyrazolyl | 115-119 |
| 1.03 | H | Cl | CH | pyrazolyl | 218-220 |
| 1.04 | H | $OC_2H_5$ | CH | pyrazolyl | |
| 1.05 | $CH_3$ | $CH_3$ | CH | pyrazolyl | |
| 1.06 | $CH_3$ | $OCH_3$ | CH | pyrazolyl | |
| 1.07 | H | $CH_3$ | CH | 1,2,4-triazolyl | 278-280 |
| 1.08 | H | $OCH_3$ | CH | 1,2,4-triazolyl | |
| 1.09 | H | $OC_2H_5$ | CH | 1,2,4-triazolyl | |
| 1.10 | H | Cl | CH | 1,2,4-triazolyl | |
| 1.11 | $CH_3$ | $CH_3$ | CH | 1,2,4-triazolyl | |
| 1.12 | $CH_3$ | $OCH_3$ | CH | 1,2,4-triazolyl | |
| 1.13 | H | $CH_3$ | CH | imidazolyl | 255 (decomp.) |
| 1.14 | H | $OCH_3$ | CH | imidazolyl | 223-25 |
| 1.15 | H | $OC_2H_5$ | CH | imidazolyl | |
| 1.16 | H | Cl | CH | imidazolyl | |
| 1.17 | H | $CH_3$ | N | pyrazolyl | 188-92 |
| 1.18 | H | $OCH_3$ | N | pyrazolyl | 154-157 |
| 1.19 | $CH_3$ | $OCH_3$ | N | pyrazolyl | |
| 1.20 | H | $CH_3$ | N | 1,2,4-triazolyl | |
| 1.21 | H | $OCH_3$ | N | 1,2,4-triazolyl | |
| 1.22 | $CH_3$ | $OCH_3$ | N | 1,2,4-triazolyl | |
| 1.23 | H | $CH_3$ | N | imidazolyl | |
| 1.24 | H | $OCH_3$ | N | imidazolyl | 245 (decomp.) |

TABLE 2

(Ia)

| Comp. no. | R¹ | R⁶ | R⁷ | X | Y | Z | M.p. [°C.] |
|---|---|---|---|---|---|---|---|
| 2.01 | $CO_2CH_3$ | O | H | $CH_3$ | CH | pyrazolyl | 199-202 |
| 2.02 | $CO_2CH_3$ | O | H | $OCH_3$ | CH | pyrazolyl | 180-182 |
| 2.03 | $CO_2CH_3$ | O | H | Cl | CH | pyrazolyl | |
| 2.04 | $CO_2CH_3$ | O | $CH_3$ | $CH_3$ | CH | pyrazolyl | |
| 2.05 | $CO_2C_2H_5$ | O | H | $CH_3$ | CH | pyrazolyl | |
| 2.06 | $CO_2CH_3$ | O | H | $CH_3$ | N | pyrazolyl | 181-183 |
| 2.07 | $CO_2CH_3$ | O | H | $OCH_3$ | N | pyrazolyl | 158-162 |
| 2.08 | $CO_2CH_3$ | O | $CH_3$ | $OCH_3$ | N | pyrazolyl | |
| 2.09 | $CO_2CH_3$ | O | H | $CH_3$ | CH | 1,2,4-triazolyl | 227-230 |
| 2.10 | $CO_2CH_3$ | O | H | $OCH_3$ | CH | 1,2,4-triazolyl | |
| 2.11 | $CO_2CH_3$ | O | H | Cl | CH | 1,2,4-triazolyl | |
| 2.12 | $CO_2CH_3$ | O | $CH_3$ | $OCH_3$ | CH | 1,2,4-triazolyl | |
| 2.13 | $CO_2CH_3$ | O | H | $CH_3$ | N | 1,2,4-triazolyl | |
| 2.14 | $CO_2CH_3$ | O | H | $OCH_3$ | N | 1,2,4-triazolyl | |
| 2.15 | $CO_2CH_3$ | O | $CH_3$ | $OCH_3$ | N | 1,2,4-triazolyl | |
| 2.16 | $CO_2CH_3$ | O | H | $CH_3$ | CH | imidazolyl | 164-166 |
| 2.17 | $CO_2CH_3$ | O | H | $OCH_3$ | CH | imidazolyl | 193-196 |
| 2.18 | $CO_2CH_3$ | O | H | $CH_3$ | N | imidazolyl | |
| 2.19 | $CO_2CH_3$ | O | H | $OCH_3$ | N | imidazolyl | 170-174 |
| 2.20 | Cl | O | H | $CH_3$ | CH | pyrazolyl | 159-163 |
| 2.21 | Cl | O | H | $OCH_3$ | CH | pyrazolyl | 197-198 |
| 2.22 | Cl | O | H | Cl | CH | pyrazolyl | 240-243 |
| 2.23 | Cl | O | H | $CH_3$ | N | pyrazolyl | 205-207 |
| 2.24 | Cl | O | H | $OCH_3$ | N | pyrazolyl | 180-182 |
| 2.25 | Cl | O | H | $CH_3$ | CH | 1,2,4-triazolyl | 206-207 |
| 2.26 | Cl | O | H | $OCH_3$ | CH | 1,2,4-triazolyl | |
| 2.27 | Cl | O | H | $CH_3$ | N | 1,2,4-triazolyl | |
| 2.28 | Cl | O | H | $OCH_3$ | N | 1,2,4-triazolyl | |
| 2.29 | Cl | O | H | $CH_3$ | CH | imidazolyl | 200-202 |
| 2.30 | Cl | O | H | $OCH_3$ | CH | imidazolyl | |
| 2.31 | Cl | O | H | $OCH_3$ | N | imidazolyl | 194-196 |
| 2.32 | $OCH_3$ | O | H | $CH_3$ | CH | pyrazolyl | |
| 2.33 | $OCH_3$ | O | H | $OCH_3$ | CH | pyrazolyl | |
| 2.34 | $OCH_3$ | O | H | $OCH_3$ | N | pyrazolyl | |
| 2.35 | $OCH_3$ | O | H | $CH_3$ | CH | 1,2,4-triazolyl | |
| 2.36 | $OCH_3$ | O | H | $OCH_3$ | CH | 1,2,4-triazolyl | |
| 2.37 | $NO_2$ | O | H | $CH_3$ | CH | pyrazolyl | |
| 2.38 | $NO_2$ | O | H | $OCH_3$ | CH | pyrazolyl | |
| 2.39 | $NO_2$ | O | H | $OCH_3$ | N | pyrazolyl | |
| 2.40 | $NO_2$ | O | H | $CH_3$ | CH | 1,2,4-triazolyl | |
| 2.41 | $SO_2CH_3$ | O | H | $CH_3$ | CH | pyrazolyl | |
| 2.42 | $SO_2CH_3$ | O | H | $OCH_3$ | CH | pyrazolyl | |
| 2.43 | $SO_2CH_3$ | O | H | $CH_3$ | CH | 1,2,4-triazolyl | |
| 2.44 | $CF_3$ | O | H | $OCH_3$ | CH | pyrazolyl | |
| 2.45 | $CF_3$ | O | H | $CH_3$ | CH | pyrazolyl | |
| 2.46 | $CF_3$ | O | H | $CH_3$ | CH | 1,2,4-triazolyl | |

TABLE 3

(Ib)

| Comp. no. | R¹ | R⁶ | R⁷ | X | Y | Z | M.p. [°C.] |
|---|---|---|---|---|---|---|---|
| 3.01 | $CO_2CH_3$ | O | H | $CH_3$ | CH | pyrazolyl | |
| 3.02 | $CO_2CH_3$ | O | H | $OCH_3$ | CH | pyrazolyl | |
| 3.03 | $CO_2CH_3$ | O | H | $CH_3$ | N | pyrazolyl | |
| 3.04 | $CO_2CH_3$ | O | H | $OCH_3$ | N | pyrazolyl | |
| 3.05 | $CO_2CH_3$ | O | H | $CH_3$ | CH | 1,2,4-triazolyl | |
| 3.06 | $CO_2CH_3$ | O | H | $OCH_3$ | CH | 1,2,4-triazolyl | |
| 3.07 | $CO_2CH_3$ | O | H | $CH_3$ | N | 1,2,4-triazolyl | |
| 3.08 | $CO_2CH_3$ | O | H | $OCH_3$ | N | 1,2,4-triazolyl | |
| 3.09 | $CO_2CH_3$ | O | H | $CH_3$ | N | imidazolyl | |
| 3.10 | $CO_2CH_3$ | O | H | $OCH_3$ | CH | imidazolyl | |

TABLE 4

$$\text{(Ic)}$$

Structure: thiophene-R¹ with SO₂NH-C(=R⁶)-N(R⁷)- linked to a pyrimidine/triazine ring with substituents X, Y, Z.

| Comp. no. | R¹ | R⁶ | R⁷ | X | Y | Z | M.p. [°C] |
|---|---|---|---|---|---|---|---|
| 4.01 | CO₂CH₃ | O | H | CH₃ | CH | pyrazolyl | |
| 4.02 | CO₂CH₃ | O | H | OCH₃ | CH | pyrazolyl | |
| 4.03 | CO₂CH₃ | O | H | CH₃ | N | pyrazolyl | |
| 4.04 | CO₂CH₃ | O | H | OCH₃ | N | pyrazolyl | |
| 4.05 | CO₂CH₃ | O | H | CH₃ | CH | 1,2,4-triazolyl | |
| 4.06 | CO₂CH₃ | O | H | OCH₃ | CH | 1,2,4-triazolyl | |
| 4.07 | CO₂CH₃ | O | H | CH₃ | N | 1,2,4-triazolyl | |
| 4.08 | CO₂CH₃ | O | H | OCH₃ | N | 1,2,4-triazolyl | |
| 4.09 | CO₂CH₃ | O | H | CH₃ | N | imidazolyl | |
| 4.10 | CO₂CH₃ | O | H | OCH₃ | CH | imidazolyl | |

The N-arylsulfonyl-N′-pyrimidyl-(triazinyl)-ureas of the formula I, or herbicidal agents containing them, may be applied for instance in the form of directly sprayable solutions, powders, suspensions (including high-percentage aqueous, oily or other suspensions), dispersions, emulsions, oil dispersions, pastes, dusts, broadcasting agents, or granules, by spraying, atomizing, dusting, broadcasting or watering. The forms of application depend entirely on the purpose for which the agents are being used, but they must ensure as fine a distribution of the active ingredients according to the invention as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as toluene, xylene, paraffin, tetrahydronaphthalene, alkylated naphthalenes and their derivatives such as methanol, ethanol, propanol, butanol, cyclohexanol, cyclohexanone, chlorobenzene, isophorone, etc., and strongly polar solvents such as N,N-dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of active ingredient.

The active ingredients, or herbicidal agents containing them, may be applied pre- or (preferably) postemergence. If certain crop plants tolerate the active ingredients less well, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

The amounts applied depend on the time of year, the plants to be combated and their growth stage, and vary from 0.002 to 1, and preferably from 0.005 to 0.5, kg/ha.

In view of the spectrum of weeds that can be combated, the tolerance of the active ingredients by crop plants, and in view of the numerous application methods available, the compounds I according to the invention may be used in a large number of crops for removing unwanted plant growth. The following may be mentioned by way of example:

| Botanical name | Common name |
|---|---|
| *Ananas comosus* | pineapples |
| *Arachis hypogaea* | peanuts (groundnuts) |
| *Asparagus officinalis* | asparagus |
| *Avena sativa* | oats |
| *Beta vulgaris* spp. *altissima* | sugarbeets |
| *Beta vulgaris* spp. *rapa* | fodder beets |
| *Beta vulgaris* spp. *esculenta* | table beets, red beets |
| *Brassica napus* var. *napus* | rapeseed |
| *Brassica napus* var. *napobrassica* | swedes |
| *Brassica napus* var. *rapa* | turnips |
| *Brassica rapa* var. *silvestris* | |
| *Camellia sinensis* | tea plants |
| *Carthamus tinctorius* | safflower |
| *Carya illinoinensis* | pecan trees |
| *Citrus limon* | lemons |
| *Citrus maxima* | grapefruits |
| *Citrus reticulata* | mandarins |
| *Citrus sinensis* | orange trees |
| *Coffea arabica* (*Coffea canephora, Coffea liberica*) | coffee plants |
| *Cucumis melo* | melons |
| *Cucumis sativus* | cucumbers |
| *Cynodon dactylon* | Bermudagrass |
| *Elais guineensis* | oil palms |
| *Fragaria vesca* | strawberries |
| *Glycine max* | soybeans |

-continued

| Botanical name | Common name |
| --- | --- |
| Gossypium hirsutum (Gossypium arboreum, Gossypium herbaceum, Gossypium vitifolium) | cotton |
| Helianthus annuus | sunflowers |
| Helianthus tuberosus | Jerusalem artichoke |
| Hevea brasiliensis | rubber plants |
| Hordeum vulgare | barley |
| Humulus lupulus | hops |
| Ipomoea batatas | sweet potatoes |
| Juglans regia | walnut trees |
| Lactuca sativa | lettuce |
| Lens culinaris | lentils |
| Linum usitatissimum | flax |
| Lycopersicon lycopersicum | tomatoes |
| Malus spp. | apple trees |
| Manihot esculenta | cassava |
| Medicago sativa | alfalfa (lucerne) |
| Mentha piperita | peppermint |
| Musa spp. | banana plants |
| Nicotiana tabacum (N. rustica) | tobacco |
| Olea europaea | olive trees |
| Oryza sativa | rice |
| Phaseolus lunatus | limabeans |
| Phaseolus mungo | mungbeans |
| Phaseolus vulgaris | snapbeans, green beans, dry beans |
| Pennisetum glaucum | pearl millet |
| Petroselinum crispum spp. tuberosum | parsley |
| Picea abies | Norway spruce |
| Abies alba | fir trees |
| Pinus spp. | pine trees |
| Pisum sativum | English peas |
| Prunus avium | cherry trees |
| Prunus domestica | plum trees |
| Prunus dulcis | almond trees |
| Prunus persica | peach trees |
| Pyrus communis | pear trees |
| Ribes sylvestre | redcurrants |
| Ribes uva-crispa | gooseberries |
| Ricinus communis | castor-oil plants |
| Saccharum officinarum | sugar cane |
| Secale cereale | rye |
| Sesamum indicum | sesame |
| Solanum tuberosum | Irish potatoes |
| Sorghum bicolor (s. vulgare) | sorghum |
| Theobroma cacao | cacao plants |
| Triticum aestivum | wheat |
| Vaccinium corymbosum | blueberries |
| Vaccinium vitis-idaea | cranberries |
| Vicia faba | tick beans |
| Vigna sinensis (V. unguiculata) | cow peas |
| Vitis vinifera | grapes |

To increase the spectrum of action and to achieve synergistic effects, the N-arylsulfonyl-N'-pyrimidyl-(triazinyl)-ureas of the formula I may be mixed with each other or mixed and applied together with numerous representatives of other herbicidal or growth-regulating active ingredient groups. Examples of suitable mixture components are diazines, 4H-3,1-benzoxazine derivatives, benzothiadiazinones, 2,6-dinitroanilines, N-phenylcarbamates, thiolcarbmates, halocarboxylic acids, triazines, amides, ureas, diphenyl ethers, triazinones, uracils, benzofuran derivatives, cyclohexane-1,3-dione derivatives, etc.

It may also be useful to apply the compounds of the formula I, either alone or in combination with other herbicides, in admixture with other crop protection agents, e.g., agents for combating pests or phytopathogenic fungi or bacteria. The compounds may also be mixed with solutions of mineral salts used to remedy nutritional or trace element deficiencies. Non-phytotoxic oils and oil concentrates may also be added.

USE EXAMPLES

The herbicidal action of the compounds of the formula I on the growth of test plants is illustrated in the following greenhouse experiments.

The vessels employed were plastic flowerpots having a volume of 300 cm$^3$, and which were filled with a sandy loam containing about 3.0% humus. The soybean plants were grown in a peat-enriched substrate. The seeds of the test plants were sown shallow, and separately, according to species. For the preemergence treatment, the active ingredients were applied to the surface of the soil immediately after the seeds had been sown. The compounds were emulsified or suspended in water as vehicle, and sprayed through finely distributing nozzles. The application rate was 0.06 kg of active ingredient per hectare. After the agents had been applied, the vessels were lightly sprinkler-irrigated to induce germination and growth. Transparent plastic covers were then placed on the vessels until the plants had taken root. The cover ensured uniform germination of the plants, insofar as this was not impaired by the active ingredients.

For the postemergence treatment, the plants were first grown in the vessels to a height of from 3 to 15 cm, depending on growth form, before being treated. For this treatment, either plants which had been sown directly in the posts and grown there were selected, or plants which had been grown from seedlings and were transplanted to the pots a few days before treatment. The application rates for postemergence treatment varied and were for example 0.0075, 0.06, 0.125 and 0.25 kg of active ingredient per hectare. No covers were placed on the vessels in this method.

The pots were set up in the greenhouse—species from warmer areas at from 20° C. to 35° C., and species from moderate climates at 10° to 20° C. The experiments were run for 2 to 4 weeks. During this period, the plants were tended and their reactions to the various treatments assessed. The scale used for assessment was 0 to 100, 0 denoting no damage or normal growth, and 100 denoting nonemergence or complete destruction of at least the visible plant parts. The influence of the treatment is assessed visually against the untreated control.

The plants used in the greenhouse experiments were *Abutilon theophrasti, Amaranthus retroflexus, Beta vulgaris, Chenopodium album, Chrysanthemum coronarium, Cyperus esculentus, Cyperus iria, Echinochloa crus-gelli, Glycine max., Gossypium hirsutum, Helianthus annuus, Lamium amplexicaule, Leptochloa fascicularis, Sesbania exaltata, Solanum nigrum, Sorghum halepense, Triticum aestivum,* Veronica spp., and *Zea mays.*

These experiments show that low application rates of the active ingredients of the formula selected by way of example have a good herbicidal action, making these compounds suitable for selectively combating unwanted plants.

Preemergence application:

At a rate of 0.25 kg/ha, compound no. 2.09 selectively combated unwanted grassy and broadleaved plants while causing only slightly growth damage to the crop plants soybeans and cotton. Compound no. 2.31 is, for instance, excellently tolerated by many crop plants and is suitable for selectively combating grassy plants preemergence.

Postemergence application:

Compound no. 2.09 effectively combated grassy and broadleaved plants without causing any damage whatsoever to soybean plants.

Compound no. 2.07 is suitable for combating grassy plants in cotton, whereas compound no. 2.02 has a good herbicidal action on a broad spectrum of various plants selected by way of example.

Sedges, for example *Cyperus iria*, are well combated with compounds nos. 2.02, 2.01, 2.17, 2.06 and 2.23.

At a rate of 0.125 kg/ha, compound no. 2.31 selectively combated broadleaved weeds and Cyperaceae in sunflowers, the active ingredient being only slightly toxic in this crop.

We claim:

1. N-arylsulfonyl-N'-pyrimidylureas of the formula

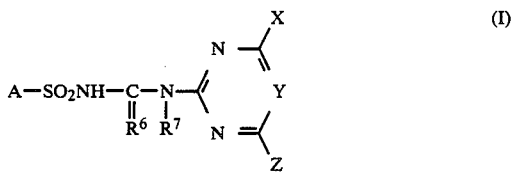

where A is a radical of the formula

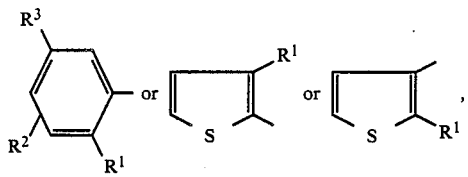

where $R^1$ is hydrogen, halogen, cyano, nitro, $C_1$–$C_4$-haloalkyl, $C_1$–$C_4$-alkyl, $C_1$–$C_4$-alkoxy, CO—$R^4$, S(O)$_m$— $C_1$–$C_4$-alkyl or SO$_2$$R^5$, $R^2$ is hydrogen, halogen, methyl, ethyl, methoxy or ethoxy, $R^3$ is hydrogen, halogen, nitro or methoxy, $R^4$ is hydrogen, $C_1$–$C_4$-alkyl, $C_1$–$C_5$-alkoxy, $C_3$–$C_5$-alkenyloxy, $C_3$–$C_5$-alkynyloxy, $C_1$–$C_5$-alkylthio, phenoxy, benzyloxy or $C_1$–$C_5$-alkoxy which is substituted by 1 to 3 halogen atoms or $C_1$–$C_3$-alkoxy, $R^5$ $C_1$–$C_4$-alkoxy, phenoxy or benzyloxy, each of which is unsubstituted or substituted by 1 to 3 halogen atoms, m is one of the integers 0, 1 and 2, $R^6$ is oxygen or sulfur, $R^7$ is hydrogen or $C_1$–$C_3$-alkyl, X is $C_1$–$C_3$-alkyl, $C_1$–$C_3$-haloalkyl, $C_1$–$C_3$-alkoxy, $C_1$–$C_3$-haloalkoxy, $C_1$–$C_3$-alkyl-thio or halogen, Y is the methyne group —CH= and Z is pyrazolyl, triazolyl or imidazolyl linked via nitrogen, and salts thereof.

2. N-arylsulfonyl-N'-pyrimidyl-ureas of the formula I as set forth in claim 1, where A is unsubstituted or substituted phenyl.

3. N-arylsulfonyl-N'-pyrimidyl-ureas of the formula I as set forth in claim 1, where $R^6$ is oxygen.

4. N-arylsulfonyl-N'-pyrimidyl-ureas of the formula I as set forth in claim 1, where $R^3$ is hydrogen.

5. N-arylsulfonyl-N'-pyrimidyl-ureas of the formula I as set forth in claim 1, where Z is pyrazolyl, 1,2,4-triazolyl, 1,2,3-triazolyl or imidazolyl linked via a nitrogen atom.

6. N-arylsulfonyl-N'-pyrimidyl-ureas of the formula I as set forth in claim 1, where A is 2-methoxycarbonylphenyl, $R^6$ is oxygen, $R^7$ is hydrogen, X is methyl, and Z is 1,2,4-triazolyl.

7. A process for combating the growth of unwanted plants, wherein the plants and/or their habitat are treated with a herbicidally effective amount of an N-arylsulfonyl-N'-pyrimidyl-urea of the formula I as set forth in claim 1.

8. A herbicidal composition which comprises: an inert carrier or diluent and a herbicidally effective amount of an N-arylsulfonyl-N'-pyrimidyl-urea of the formula as set forth in claim 1.

* * * * *